(12) United States Patent
Blum et al.

(10) Patent No.: US 6,656,742 B2
(45) Date of Patent: Dec. 2, 2003

(54) METHOD FOR IMPROVING THE MEASUREMENT ACCURACY OF SENSORS

(75) Inventors: Uwe Blum, Markkleeberg (DE); Franz Drobner, Munich (DE); Peter Boll, Weilheim (DE)

(73) Assignee: pe$^s$ Gesellschaft fuer Medizinische Diagnosesysteme mbH, Markkleeberg (DE)

( * ) Notice: Subject to any disclaimer, the term of this patent is extended or adjusted under 35 U.S.C. 154(b) by 55 days.

(21) Appl. No.: 10/081,621

(22) Filed: Feb. 21, 2002

(65) Prior Publication Data

US 2003/0157726 A1 Aug. 21, 2003

(51) Int. Cl.$^7$ .............................................. G01N 21/64
(52) U.S. Cl. ................................................ 436/172
(58) Field of Search .................... 436/172, 164, 436/8; 422/82.11; 250/458.1, 459.1

(56) References Cited

U.S. PATENT DOCUMENTS

| | | | | |
|---|---|---|---|---|
| 5,525,466 A | * | 6/1996 | Slovacek et al. .............. | 435/6 |
| 5,856,203 A | | 1/1999 | Robinson et al. | |
| 5,872,713 A | * | 2/1999 | Douglas et al. ............... | 702/85 |
| 6,315,951 B1 | * | 11/2001 | Markart ....................... | 422/61 |
| 6,562,625 B2 | * | 5/2003 | Modzelewski et al. ....... | 436/44 |

FOREIGN PATENT DOCUMENTS

| | | |
|---|---|---|
| DE | 26 38 398 | 4/1977 |
| DE | 28 00 225 | 7/1978 |
| DE | 29 02 776 | 8/1979 |
| DE | 196 39 226 | 3/1998 |
| DE | 197 81 162 | 3/1999 |
| DE | 198 11 622 | 9/1999 |
| DE | 692 30 420 | 8/2000 |
| EP | 0 517 516 | 12/1992 |
| EP | 1 031 828 | 8/2000 |
| WO | 98/19159 | 5/1998 |

* cited by examiner

Primary Examiner—Jeffrey Snay
(74) Attorney, Agent, or Firm—Jordan and Hamburg LLP

(57) ABSTRACT

Fluorescing reference material is used for calibration purposes for improving the measurement accuracy of sensors, especially biosensors, which use fluorescence radiation for determination of signals, the sensors each comprising a waveguide having at least one wave propagation surface as assay, a reactant being supported on the surface, the reactant comprising a species of molecule and being bound to an analytical material within a test medium, the waveguide transmitting an output emission radiation signal when it receives a radiation access signal.

1 Claim, 1 Drawing Sheet

$$\alpha = \frac{I_{FS}}{I_0}$$

Figure 1:
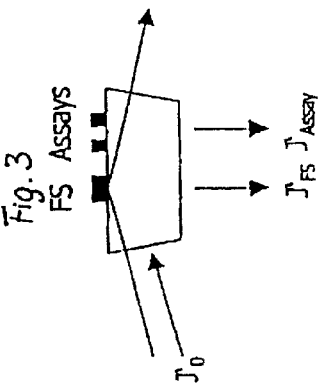

$$\alpha = \frac{J_{FS}}{J_0} \qquad \beta = \frac{J_{Assay}}{J_0}$$

$$\beta = \alpha * \frac{J_{Assay}}{J_{FS}}$$

$$\beta = \alpha * \frac{J_{Assay}}{J_{FS}}$$

Measurement of β

$$\beta = f(c)$$

→ Result c (mol/l)

α is sensor specific and is measured over the whole batch with the highest possible precision

METHOD FOR IMPROVING THE MEASUREMENT ACCURACY OF SENSORS

The invention relates to a method for improving the measurement accuracy of sensors, especially of biosensors, which use fluorescence radiation for the determination of the signals, comprising a waveguide with at least one wave propagation surface as assay, which contains a reactant, which consists of a species of molecule, which is bound to an analytical material within test medium, and of a fluorescing reference material, which is used for the calibration, the waveguide transmitting an output emission radiation signal when it receives a radiation access signal.

The DE 69230420 T2 discloses a sensor for evanescent waves for receiving one or more electromagnetic radiation input signals and for emitting at least two output signals. The assay of the sensors consists of a waveguide with at least one wave propagation surface, which contains a coating, which consists of a reagent of a molecular nature and is bound to an analytical material within a test medium. On the wave propagation surface, there is a fluorescing reference material. Upon receiving one or more radiation input signals, the waveguide transmits an input emission radiation signal with a first wavelength, which is characteristic for at least one analytical binding reaction, and a separate output emission radiation signal emanating from the reference material with a second wavelength in such a manner, that the reference material sees to the normalization and/or calibration of the sensor.

During use, the invention enables the reference material as well as the analyte to be detected, so that an agent is made available for the normalization and calibration of the system with respect to any deviations in the sensor and in the efficiency of the instrument-sensor combination, which affect the signal access and the pick up of the signal. Since the known output signal from the reference material is affected in the same way as the signal from the analyte by any geometric deviations and surface irregularities in the sensor, the ratio of the output of the analyte signal to the output of the reference signal makes available a value, which varies only with differences in the analyte and not with differences between sensors. In order to avoid difficulties during the analysis of the output signals, the reference material can be selected so that it makes available an output signal wavelength, which is different and/or easily differentiated from the signal, which indicates the analyte. The suitability of the sensor for the reference system is associated with high manufacturing costs. The DE 69302273 T2 shows a method for improving the accuracy of measurement in optical biosensors essays using the damped wave technique, devices for use with such a method and the use. In addition to the ligand in the sample, an amount of directly or indirectly immobilized species ("the reference reagent") is added, which, independently of the amount of the ligand, in the sample, leads to an increase to a detectable signal ("the reference signal") on the measurement surface, the reference signal being measured by a method before, during or after the incubation of the sample. This invention implies a high technical expenditure for the equipment using this method, which evaluates reference signals for improving the accuracy of measurements of the biosensors.

The DE 19781162 T1 relates to an apparatus for determining the chemical and biological components of body fluids, especially for self-monitoring blood sugar concentrations of patients with diabetes, using test instruments for measuring the analyte activity on test strips, which are impregnated with suitable reagents. A calibration strip can be connected detachably at the test instrument for communicating electronically with a microprocessor, which controls the operation of the test instrument. The calibration chip contains calibration information, which is unambiguously specific for the reagent, which is prepared with a special set of test strips, which are supplied with the calibration strip. In this way, it is possible to compensate for batch differences in the reagent and it is not necessary for the user to enter or contribute this information. This minimizes errors and facilitates the use and accuracy of the test instrument. In particular, the use of a wrong batch of test strip is precluded. It is a disadvantage that these calibration chips improve the reliability of handling the detection equipment and not the quality of the determination of chemical and biological components in body fluids. The DE 199639226 A1 shows a portable measuring device for determining the concentration of at least one substance in a body fluid by means of evaluating a test strip. However, the characteristic curve of the test strips of this type differ from batch to batch. A calibration curve must therefore be provided for each batch and entered into the measuring device, in order to ensure a reliable measurement. However, operators frequently forget to pre-set the measuring device. In order to avoid this, a code reading device is disposed in the housing of the measuring device in such a manner that, when a cassette is inserted in the housing, it can read a code on the cassettes. The reading device may be formed, for example, by a bar code reader. This measuring device works with a calibrated test strip, however, without improving the accuracy of the measurements.

In it is an object of the invention to develop a method for improving the measuring accuracy of sensors, especially of biosensors, which use fluorescence radiation to determine the signals, comprising a waveguide with at least one wave propagation surface as assay, which contains a reactant, which consists of one species of molecules, which is bound to an analytical material within a test medium, and a fluorescing reference material, the waveguide transmitting an output emission radiation signal when it receives a radiation access signal, for which method the manufacturing costs are reduced and the sensors can be produced with an improved measuring accuracy.

Pursuant to the invention, this objective is accomplished owing to the fact that at each sensor of a batch, a fluorescence standards strip is affixed as reference material, this strip being disposed at the sensor next to the assay or spatially separated therefrom subsequently, for each affixed fluorescence standard strip (FS) of the sensor batch, the fluorescence signal ($I_{FS}$) is measured by means of a process fluorimeter and a correction factor ($\alpha$) of the fluorescence signal ($I_{FS}$) related to a nominal batch value ($I_o$), is formed for each sensor;

$$\alpha = I_{FS}/I_o$$

the internal correction value $\alpha$ of the sensor is written on a data storage medium, which is affixed to each sensor, or filed in an appropriate data base;

subsequently, the assay is calibrated, sensors being taken at random from a batch of sensors and measured with calibrators with known concentrations of analyte, in order to determine the fluorescence signals as a function of the analyte concentration for each essay;

subsequently, the correction value $\alpha$ is read from each data storage medium of the sensors or taken from the database and a ratio β of the fluorescence intensity of the assay ($J_{Assay}$) to that of the fluorescence standards strip ($J_{FS}$) is formed $$\beta = \alpha (J_{Assay}/J_{FS})$$

a calibration curve of the sensor is determined from the ratio β for the individual analyte concentrations of each individual sensor of the batch and affixed to the sensor as information or read into a database, for the measurement of an analyte concentration (c) of an unknown sample, the measured fluorescence signals from the assay ($J'_{Assay}$) and from the fluorescence standards strip ($J'_{FS}$) are related to one another and multiplied by the correction value α of the sensor, in order to obtain the ratio β, in order to determine the concentration of analyte (C) of the unknown sample from the magnitude of β and of the lot-specific calibration curve f(c) enclosed with the sensor.

Figure 2:
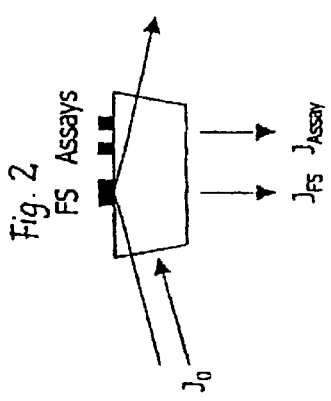
Figure 3:
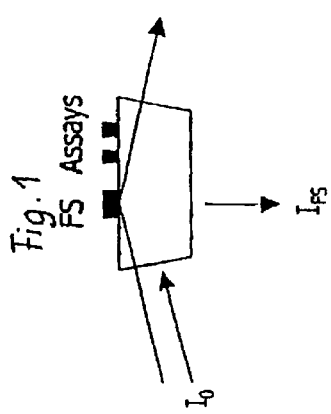
Figure 4:
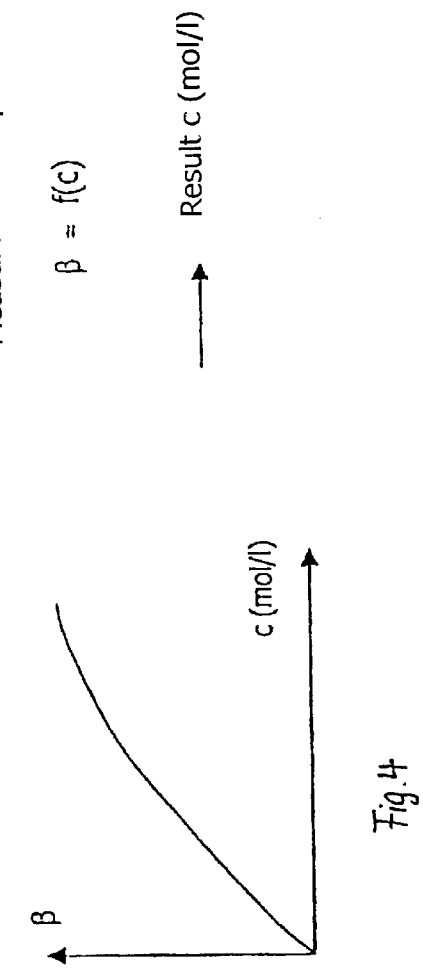

In the following, the invention is described in greater detail by means of an example and a drawing, in which FIG. 1 shows a diagrammatic representation of the determination of the correction value α, FIG. 2 shows a diagrammatic representation of the calibration of the assay, FIG. 3 shows a diagrammatic representation of a sample measurement and FIG. 4 shows a calibration curve of a sensor.

A sensor consists of a waveguide with at least one wave propagation surface as assay, which contains a reactant, which consists of one species of molecules, which is bound to an analytical material within a test medium, and of a fluorescing reference material. Upon receiving radiation access signals, the waveguide transmits an outlet emission radiation emission signal.

During the production of a batch of sensors, the reactants for the assay, as well as a fluorescence standard strip FS as a fluorescing reference material are affixed on the measurement surface or on a position spatially separated therefrom. Subsequently the fluorescence standard strips FS of all sensors of a batch are measured with a very precise process fluorimeter and an individual correction factor α for each sensor is formed as in FIG. 1 in that the fluorescence signal $I_{FS}$ of the fluorescence standard strip FS is related to the nominal batch value $I_o$. Subsequently, the internal correction value α of the sensor is written on a data storage medium, which is affixed to each sensor, or filed in an appropriate database. Subsequently, as shown in FIG. 2, the assay is calibrated, sensors being taken at random from the sensor batch and measured with calibrators with known concentrations of analyte, in order to determine the fluorescence signals $J_{FS}$ as a function of the analyte concentration C for each essay $J_{Assay}$. Subsequently, the correction value α is read from the data storage medium of each sensor or taken from the database and a ratio β of the fluorescence intensity of the assay $J_{Assay}$ to that of the fluorescence standards strip $J_{FS}$ is formed. A calibration curve f(c), FIG. 4, for the sensor is determined from the ratios β for the individual analyte concentrations of each individual sensor of the batch of sensors and affixed to the sensor as information or read into the database. During the analysis of sample material FIG. 3, the unknown concentration C of the analyte of which is to be measured, the sensor-specific correction value α is read from the data storage medium of the sensor or from the sensor during the measurement by the user. The fluorescence signals, measured from the assay $J'_{Assay}$ and the fluorescent standard strip $J'_{FS}$ are related to one another and multiplied by the correction value α of the sensor, so that the ratio β is obtained. Subsequently the analyte concentration of the unknown sample C is determined from the quantity β and the batch-specific correction curve f(c), FIG. 4, which is enclosed with the sensor.

What is claimed is:

1. Method for improving measurement accuracy of sensors which use fluorescence radiation for determination of signals, the sensors each comprising a waveguide having at least one wave propagation surface as assay, a reactant supported on said surface, the reactant comprising a species of molecule and being bound to an analytical material within a test medium, the method including using a fluorescing reference material for calibration purposes, the waveguide transmitting an output emission radiation signal when it receives a radiation access signal, wherein to each sensor of a production batch consisting of a plurality of sensors a fluorescence standards strip is affixed as reference material, subsequently, for each affixed fluorescence standards strip of the sensor batch, a fluorescence signal $I_{FS}$ is measured by means of a process fluorimeter and a value of a correction factor α of the fluorescence signal $I_{FS}$ related to a nominal batch value $I_o$ is obtained for each sensor according to equation (1)

$$\alpha = I_{FS}/I_o \tag{1}$$

the correction value α of the sensor is written on a data storage medium which is affixed to each sensor or entered in an appropriate data base;

subsequently, the assay is calibrated, sensors being taken at random from the batch of sensors and measured with calibrators with known concentrations of analyte, in order to determine the fluorescence signals as a function of the analyte concentration for each assay $J_{Assay}$;

subsequently, the correction value α is read from each data storage medium of the sensors or taken from the database and a ratio β of the fluorescence intensity of the assay $J_{Assay}$ to that of the fluorescence standards strip $J_{FS}$ is obtained according to equation (2)

$$\beta = \alpha (J_{Assay}/J_{FS}) \tag{2}$$

a calibration curve of the sensor is determined from the ratio β for the individual analyte concentrations of each individual sensor of the batch and affixed to the sensor as information or entered into a database;

for the measurement of an analyte concentration of an unknown sample, the measured fluorescence signals from the assay and from the fluorescence standards strip are related to one another and multiplied by the correction value α of the sensor, in order to obtain the ratio β, in order to determine the concentration of analyte of the unknown sample from the magnitude of β and of the calibration curve for the sensor.

* * * * *